US007015176B2

(12) United States Patent
Bailey, III et al.

(10) Patent No.: US 7,015,176 B2
(45) Date of Patent: Mar. 21, 2006

(54) PROCESS FOR THE SYNTHESIS OF ARYL SULFURPENTAFLUORIDES

(75) Inventors: Wade H. Bailey, III, Emmaus, PA (US); William J. Casteel, Jr., Emmaus, PA (US); Reno J. Pesaresi, Easton, PA (US); Frank M. Prozonic, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/453,743

(22) Filed: Jun. 3, 2003

(65) Prior Publication Data
US 2004/0249209 A1   Dec. 9, 2004

(51) Int. Cl.
C07C 51/245 (2006.01)
C07C 209/00 (2006.01)
C07C 381/00 (2006.01)
C07C 331/00 (2006.01)
C07C 317/00 (2006.01)

(52) U.S. Cl. .................... 502/527; 564/417; 564/440; 568/74

(58) Field of Classification Search .............. 568/74; 564/440, 417; 502/527
See application file for complete search history.

(56) References Cited

U.S. PATENT DOCUMENTS

| 3,073,861 A | 1/1963 | Raach | 260/552 |
| 3,219,690 A | 11/1965 | Sheppard | 260/515 |
| 4,766,243 A | 8/1988 | Fifolt | 564/414 |
| 5,741,935 A * | 4/1998 | Bowden et al. | 568/74 |

FOREIGN PATENT DOCUMENTS

| WO | WO9422817 | 10/1994 |
| WO | WO 97/05106 | 2/1997 |
| WO | WO9705106 | 2/1997 |
| WO | WO 99/22857 | 5/1999 |

OTHER PUBLICATIONS

*Discovering New Roles for Fluorine: From Enzymes to Microlithography*, 16th Winter Fluorine Conference (2003).
R. D. Bowden, et al., *A New Method for the Synthesis of Aromatic Sulfurpentafluorides and Studies of the Stability of the Sulfurpentafluoride Group in Common Synthetic Transformations*, Tetrahedron 56 (2000), pp. 3399-3408.
H. Baba, et al., *Electrochemical Fluorination of Ethanethiol*, Bulletin of the Chemical Society of Japan, vol. 50 (10), pp. 2809-2810 (1977).
T. Abe, et al., *The Electrochemical Fluorination of Dithiols and Cyclic Sulfides*, Bulletin of the Chemical Society of Japan, vol. 46, pp. 3845-3848 (1973).
A. M. Sipyagin, et al., *Preparation of the First Ortho-Substituted Pentafluorosulfanylbenzenes*, Journal of Fluorine Chemistry, 112, pp. 287-295 (2001).
D. Viets, et al., *1,2-Bis[trifluorosulfur(IV)]tetrafluoroethane $F_2S$-$CF_2$-$SF_3$: A Bifunctional Molecule with Two Fluoroamphoteric Sulfur Centers*, Eur. J. Inorg. Chem., pp. 1035-1039 (1998).
T. Abe, *Fluorination of Perfluoroalkylsulfenyl Chlorides, Perfluorodialkyl Disulfides and Perfluorodialkyl Sulfides with Chlorine Monofluoride*, Journal of Fluroine Chemistry, 3 pp. 187-196 (1973/74).
F. A. Hohorst, et al., *Some Reactions of Bis(fluoroxy)difluoromethane, $CF_2(OF)_2$*, Inorganic Chemistry, vol. 7, No. 3, pp. 624-626 (1968).
R. E. Bailey, et al., *Reactions of Trifluoromethyl Hypofluorite with Sulfur and with Other Substances Containing Divalent Sulfur*, Inorganic Chemistry, vol. 9, No. 8, pp. 1930-1932 (1970).
S. Novick, et al., *Dialkyl- and Diaryltetrafluoropersulfuranes*, Journal of the American Chemistry Society, 95:24, pp. 8191-8192 (1973).
R. Winter, et al., *Functionalization of Pentafluoro$\lambda$,[6]-sulfanyl ($SF_5$) Olefins and Acetylenes*, American Chemical Society, pp. 129-147 (1994).
H. J. Emeleus, et al., *The Alkyl- and Aryl-substitued Fluorides of Sulphur, Selenium, Tellurium, and Iodine*, Imperial College, London, pp. 1126-1131 (1946).
D. Lentz, et al., *The -$SF_5$,-$SeF_5$, and -$TeF_5$ Groups in Organic Chemistry*, Chemistry of Hypervalent Compounds, pp. 295-325 (1999).
W. A. Sheppard, *Arysulfur Pentafluorides*, Central Research Dept. Experimental Station, E.I. DuPont de Nemours, vol. 84, pp. 3064-3072 (1962).
W. A. Sheppard, *Arylsulfur Trifluorides and Pentafluorides*, Central Research Dept. Experimental Station, E.I. DuPont de Nemours, vol. 82, pp. 4751-4752 (1960).
X. Ou, et al., *Oxidative Fluorination of S, Se and Te Compounds*, Journal of Fluorine Chemistry, 101, pp. 279-283 (2000).
R. Bowden, et al., *Selective Direct Fluorination*, F2 Chemicals Ltd.
Bowden, et al., "A New Method for the synthesis of Aromatic Sulfupentabluorides and Studies of the Stability of the Sulfurpentafluoride Group in Common Synthetic Transformations", Tetrahedron 56 (2000), pp. 3399-3408.
Chambers, et al., "Microreactors for Elements Fluorine", Chem. Commun., 1999, pp. 883-884.

* cited by examiner

Primary Examiner—Cecilia J. Tsang
Assistant Examiner—Raymond Covington
(74) Attorney, Agent, or Firm—Rosaleen P. Morris-Oskanian

(57) ABSTRACT

A process is described for the synthesis of an aryl sulfur pentafluoride compound. In one embodiment of the present invention, there is provided a process for preparing an aryl sulfurpentafluoride compound comprising: combining an at least one aryl sulfur compound with a fluorinating agent to at least partially react and form an intermediate aryl sulfurtrifluoride product; and exposing the intermediate aryl sulfurtrifluoride product to the fluorinating agent and optionally a fluoride source to at least partially react and form the aryl sulfurpentafluoride compound.

25 Claims, 1 Drawing Sheet

PROCESS FOR THE SYNTHESIS OF ARYL SULFURPENTAFLUORIDES

BACKGROUND OF THE INVENTION

Figure 1:
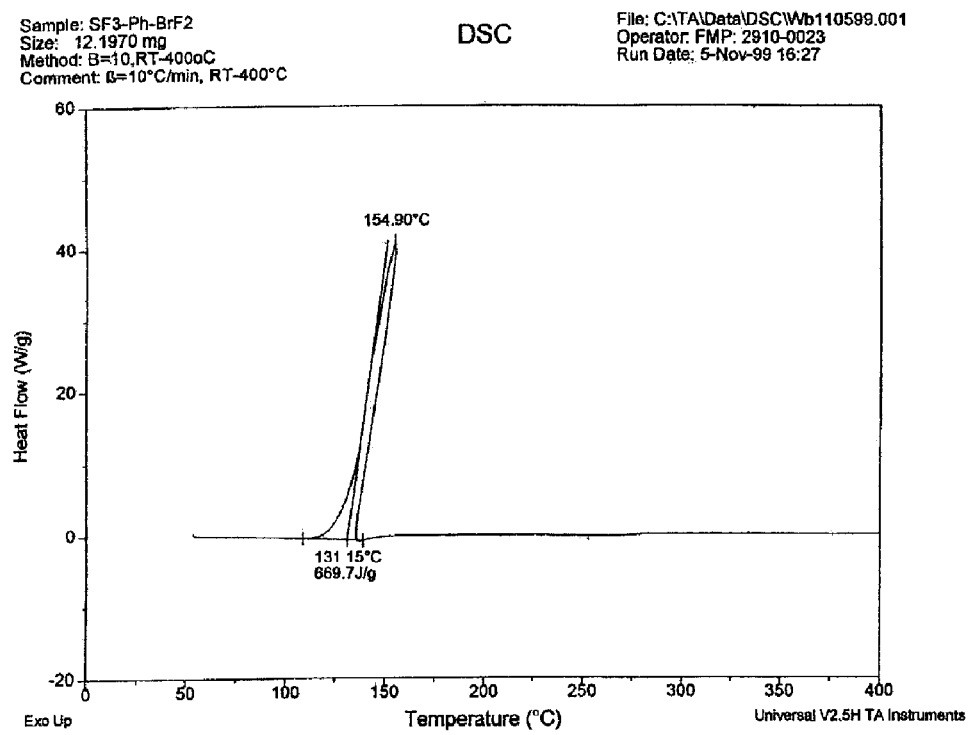

The present invention relates generally to a method for the synthesis of a sulfurpentafluoride compound. More particularly, the present invention relates generally to a method for the synthesis of an aryl sulfurpentafluoride compound.

The development of synthetic methodologies for the introduction of sulfurpentafluoride or pentafluorosulfuranyl groups ("SF$_5$") into organic compounds has been pursued with a considerable degree of interest by several research groups. It is believed that the SF$_5$ group may impart unique properties to these organic compounds that include, inter alia, low surface energy, high chemical resistance, high thermal stability, high electronegativity, hydrophobicity, and high dielectric constant. For instance, the high electronegativity value of the SF$_5$ group, 3.62 on the Pauling scale, and greater electron withdrawing ability may make it an attractive alternative for the trifluoromethyl group ("CF$_3$") found in many commercial products. Aryl sulfurpentafluoride compounds can be used to introduce one or more sulfurpentafluoride groups into an organic compound.

The prior art provides a variety of methods for the synthesis of sulfur pentafluoride compounds such as aryl sulfurpentafluoride compounds. For example, U.S. Pat. Nos. 3,073,861 and 3,219,690 and the references Sheppard, W. A., "Arylsulfur Trifluoride and Pentafluorides", *J. Am. Chem. Soc.*, 82 (1960), pp. 4751–52 and Sheppard W. A., "Arylsulfur Pentafluoride", *J. Am. Chem. Soc.*, 84 (1962), pp. 3064–72 (referred to herein collectively as Sheppard) describe a two-step method for preparing aryl sulfurpentafluoride compounds by reacting aryl disulfides or aryl sulfur trifluorides with AgF$_2$. The reported yields of this two-step method were relatively low, i.e., 5 to 35%. Other references, such as, Lentz et al., "The —SF$_5$, —SeF$_5$, and —TeF$_5$ Groups in Organic Chemistry", CHEMISTRY OF HYPERVALENT COMPOUNDS, Wiley Co., NY, N.Y. (1999), pp. 295–324; Baba, H. et al., "The Electrochemical Fluorination of Ethanethiol", *Bulletin of the Chemical Society of Japan*, Vol. 50 (10) (1977), pp. 2809–2810; Abe, T. et al., "The Electrochemical Fluorination of Dithiols and Cyclic Sulfides", *Bulletin of the Chemical Society of Japan*, Vol. 46 (1973), pp. 3845–3848 (referred to herein collectively as "Baba"); and Winter, R., et al., "Functionalization of Pentafluoro-λ-sulfanyl (SF$_5$) Olefins and Acetylenes", INORGANIC FLUORINE CHEMISTRY: TOWARD THE 21$^{ST}$ CENTURY, Thrasher and Strauss, Washington D.C. (1994), pp. 129–66, describe methods of preparing —SF$_5$ containing organics through direct reactions of organic substrates with F$_5$S• reagents, electrochemical fluorinations of organo-sulfur compounds, and functionalization of pentafluorothio acetylenes and olefins, respectively. Each of the aforementioned methods present various processing difficulties such as lack of selectivity, poor yields, over-fluorination, or painstaking purifications.

More recently, published patent application WO 94/22817 and the reference Sipyagin, A. M. et al., "Preparation of the First Ortho-Substituted Pentafluorosulfanylbenzenes", *J. of Fluorine Chem.*, Vol. 112 (2001), pp. 287–95, describe methods that improve upon Sheppard's two-step method through the use of alternate, non-aqueous solvents or the presence of copper or other metals within the reaction conditions. However, these improved methods still employ high-cost AgF$_2$ as a reagent.

Published patent application WO 97/05106, U.S. Pat. No. 5,741,935, and the reference Bowden, R. D., et al., "A New Method for the Synthesis of Aromatic Sulfurpentafluorides and Studies of the Stability of the Sulfurpentafluoride Group in Common Synthetic Transformations", *Tetrahedron* 56 (2000), pp. 3399–3408 (referred to herein collectively as Bowden) describe a commercial process for the preparation of nitrophenyl sulfurpentafluoride by treating the corresponding nitrophenyl disulfides, thiols, or sulfur trifluoride with dilute F$_2$. It appears, however, that the Bowden process is practically limited to deactivated aromatics.

The reference, Ou, X., et al., "Oxidative Fluorination of S, Se, and Te Compounds, *J. of Fluorine Chem.*, 101 (2000), pp. 279–283 (referred to herein as "Ou"), describes a method to synthesize aryl sulfurpentafluoride compounds involving the oxidative fluorination of aromatic sulfur compounds with XeF$_2$, such as that illustrated in Scheme 1. The oxidative fluorination of the sulfur atom to sulfur (VI) fluorides quickly and easily under mild conditions.

Scheme 1

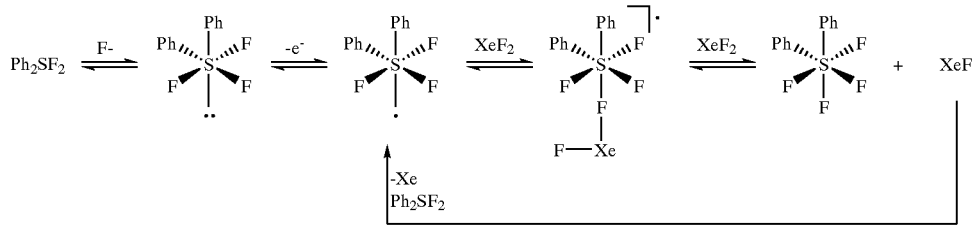

While the method of Scheme I may be convenient for small-scale laboratory preparations and studies, the cost and availability of XeF$_2$ make this method impractical for commercial production of —SF$_5$ compounds.

In addition to the Ou method, other methods for the oxidative fluorination of sulfur or sulfur-containing compounds include using gaseous fluoroxy reagents such as fluoroxytrifluoromethane ("FTM" or F$_3$COF) or bis(fluoroxy)difluoromethane ("BDM" or F$_2$C(OF)$_2$). For example, the references, Denney, D. B., et al., "Dialkyl- and Diaryltetrafluoropersulfuranes", *J. of the Am. Chem. Soc.*, Vol. 95:24, Nov. 28, 1973, pp. 8191–92, Bailey, R. E., et al., "Reactions of Trifluoromethyl Hypofluorite with Sulfur and with Other Substances Containing Divalent Sulfur", *Inorganic Chemistry*, Vol, 9, No., 8 (1970), pp. 1930–32, and Hohorst, F. A., et al., "Some Reactions of Bis(fluoroxy)difluoromethane, CF$_2$(OF)$_2$", *Inorganic Chemistry*, Vol. 7, No. 3 (1968), pp. 624–26, describe the reaction of FTM with dialkyl and diaryl sulfides to yield dialkyl and diaryl tetrafluorosulfuranes, the reaction of FTM with sulfur at room temperature to give S(II) and S(IV)fluorides, and the reaction of BDM with sulfur to yield sulfur tetrafluoride, respectively. Further, the references, Abe T. et al., "Fluorination of Perfluoroalkylsufenyl Chlorides, Perfluorodialky Disulfides and Perfluorodialkyl Sulfides with Chlorine Monofluoride", *J. of Fluorine Chem.*, Vol. 3 (1973/74), pp. 187–196 and Viets, D., et al., "1,2-Bis[trifluorosulfur(IV)tetrfluoroethane F$_3$S—CF$_2$—CF$_2$—SF$_3$" A Bifunctional Molecule with Two Fluoroamphoteric Sulfur Centers", *Eur. J. Inorg. Chem.*, Vol. 7 (1998), pp. 1035–39, describe oxidative fluorinations of sulfenyl halides but are limited to those of perfluoroalkanesulfenyl chlorides. Thus, the use of fluoroxy reagents to generate aryl sulfurpentafluoride compounds has remained unexplored.

Despite the foregoing developments, there remains a need in the art for a safe and cost-effective process to make aryl sulfurpentafluoride compounds at greater yields, higher purities, and in a single reaction vessel. Further, there is a need in the art for a synthesis method that produces a high purity aryl sulfurpentafluoride compound without the necessity of extensive purification processes.

All references cited herein are incorporated herein by reference in their entireties.

BRIEF SUMMARY OF THE INVENTION

The present invention satisfies one, if not all, of the needs in the art by providing a method for the synthesis of arylsulfur pentafluoride compounds. In one aspect of the present invention, there is provided a process for preparing an aryl sulfurpentafluoride compound having the following formula (III) comprising:

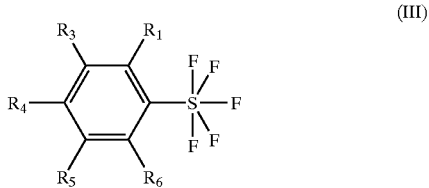

(III)

combining at least one aryl sulfur compound having a formula (Ia) or a formula (Ib) as follows:

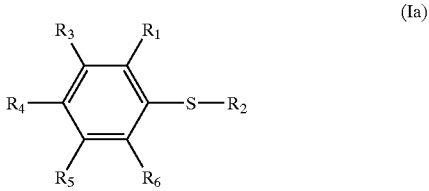

(Ia)

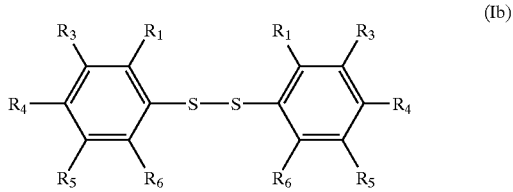

(Ib)

with a fluorinating agent to at least partially react and form an intermediate aryl sulfurtrifluoride product; and exposing the intermediate aryl sulfurtrifluoride product to the fluorinating agent and a fluoride source to at least partially react and form the aryl sulfurpentafluoride compound. In formulas (Ia), (Ib), and (III), $R_1$, $R_3$, $R_4$, $R_5$, and $R_6$ are each independently a hydrogen atom; a halogen atom; a linear alkyl group having a number of C atoms that range from 1 to 18; a branched alkyl group having a number of C atoms that range from 3 to 18; a cyclic alkyl group having a number of C atoms that range from 3 to 18; an aryl group having a number of C atoms that range from 6 to 30; an alkoxy group having a number of C atoms that range from 1 to 18; $NO_2$; a perfluoroalkyl group having a number of C atoms that range from 1 to 18; a $SF_5$; a $SO_2F$; or a CN group. In formula (Ia), $R_2$ is a hydrogen atom or a halogen atom.

In another aspect of the present invention, there is provided a process for preparing an aryl sulfurpentafluoride compound having the above formula (III) comprising: providing a mixture comprising from 1 to 70 weight percent of at least one aryl sulfur compound having the above formulas (Ia) or (Ib) and from 30 to 99 weight percent of a solvent; introducing a fluorinating agent to the mixture to form an intermediate aryl sulfurtrifluoride product; and exposing the intermediate aryl sulfurtrifluoride product to the fluorinating agent and a fluoride source to at least partially react and form the aryl sulfurpentafluoride compound.

In a further aspect of the present invention, there is provided a process of preparing an aryl sulfur pentafluoride compound having the above formula (III) comprising: combining at least one aryl sulfur compound having the above formulas (Ia) or (Ib) with a fluoroxy reagent to at least partially react and form an intermediate aryl sulfurtrifluoride product; and exposing the intermediate aryl sulfurtrifluoride product to the fluoroxy reagent to at least partially react and form the aryl sulfurpentafluoride compound.

These and other aspects of the present invention will be more apparent from the following description.

DETAILED DESCRIPTION OF THE INVENTION

This present invention provides an improved method for the synthesis of arylsulfur pentafluoride compounds. Unlike previous methods of the art, the method of the present invention uses relatively low-cost fluorinating agents of variable reactivity, with optionally a fluoride source, to prepare arylsulfur pentafluoride compounds from aryl sulfur precursor compounds. As a result of the method of the present invention, the resultant aryl sulfurpentafluoride compound is prepared in moderate to excellent yields, at improved purities and with enhanced process safety, then was attainable heretofore.

Although not intending to be bound by theory, it is believed that the present invention involves reacting at least one aryl sulfur precursor compound with one or more fluorinating agents to provide an intermediate aryl sulfurtrifluoride product which is then exposed to one or more fluorinating agents to provide an aryl sulfur pentafluoride compound. In certain preferred embodiments, the exposing step is conducted in the presence of a fluoride source. Equation I provides an example of one embodiment of the present invention wherein an aryl sulfur precursor compound having the formula (Ia) is used in the reacting step and a fluoride source is used in addition to the one or more fluorinating agents in the exposing step.

Equation I

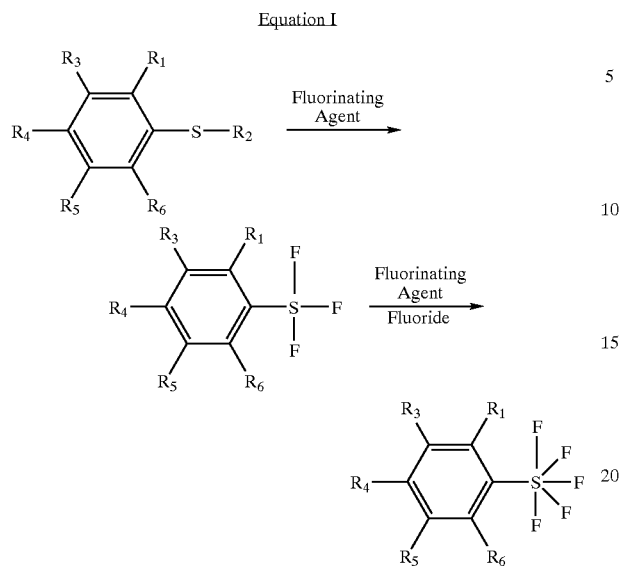

The method of the present invention provides many distinct advantages over the methods of the prior art. The method of the present invention, inter alia, avoids extensive ring fluorination, prevents the excessive formation of process-damaging HF, minimizes solvent fluorination in embodiments wherein a solvent is used, avoids high temperatures where radical fluorinations persist, avoids vigorous and uncontrolled reactions of undissolved solids with the fluorinating agent, minimizes or eliminates the formation of unstable or undesirable side-products from the oxidation of additional ring substituent groups, produces more easily purified product mixtures, and allows the fluorination of higher concentrations of precursor. Because of these distinct advantages, the present invention overcomes the difficulties of the prior art and allows for large scale, cost-effective manufacture of arylsulfur pentafluoride compounds.

As mentioned previously, the first step of the present involves the reaction of an at least one aryl sulfur precursor compound having the following formulas (Ia) or (Ib):

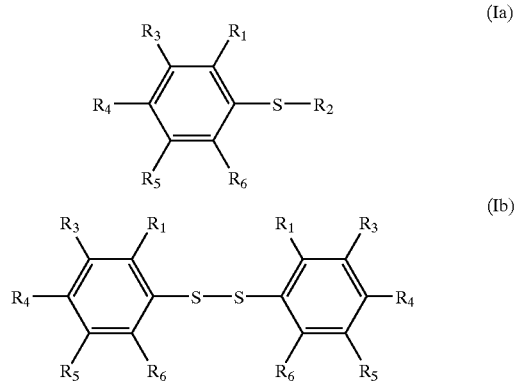

with one or more fluorinating agents, and optionally one or more fluoride sources, to form an intermediate aryl sulfurtrifluoride product having the following formula (II).

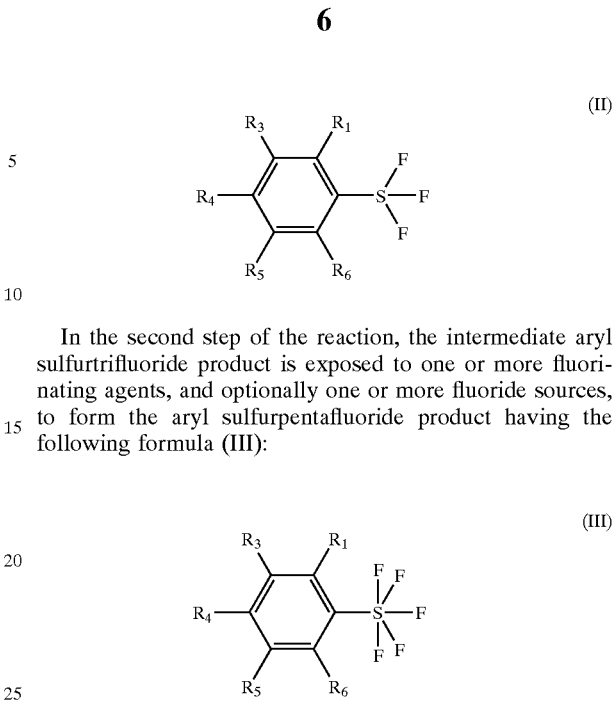

In the second step of the reaction, the intermediate aryl sulfurtrifluoride product is exposed to one or more fluorinating agents, and optionally one or more fluoride sources, to form the aryl sulfurpentafluoride product having the following formula (III):

In certain preferred embodiments of the present invention, the first and second steps of the present invention are conducted in the same reaction vessel. At least a portion of the second step is preferably conducted during at least a portion of the first step to allow for continuous processing.

In above formulas (Ia), (Ib), (II), and (III), substituents $R_1$, $R_3$, $R_4$, $R_5$, and $R_6$ are each independently a hydrogen atom; a halogen atom; an linear alkyl group having a number of C atoms that range from 1 to 18; a branched alkyl group having a number of C atoms that range from 3 to 18, preferably from 3 to 10 atoms; a cyclic alkyl group having a number of C atoms that range from 3 to 18, preferably from 4 to 10; an aryl group having a number of C atoms that range from 6 to 30; an alkoxy group having a number of C atoms that range from 1 to 18; $NO_2$; a perfluoroalkyl group having a number of C atoms that range from 1 to 18; a $SF_5$; a $SO_2F$, or a CN group. In formula (Ia), $R_2$ is a hydrogen atom or a halogen atom. The term "alkyl" as used herein also applies to alkyl moieties contained in other groups such as haloalkyl, alkaryl, or aralkyl. The term "halo" and "halogen" include fluorine, chlorine, bromine, or iodine. The term "aryl" as used herein includes rings having an aromatic character containing 6 to 30 carbon atoms, preferably from 6 to 15 carbon atoms. The term "aryl" also applies to aryl moieties that are substituted such as alkyl-substituted aryl, a partially fluorinated aryl, a fluoralkyl-substituted aryl. The term "perfluoroalkyl" includes straight chain, branched, or cyclic perfluoroalkyl groups, preferably containing from 1 to 18 carbon atoms, or more preferably from 1 to 9 carbon atoms. In certain embodiments, some of the groups may be substituted with one or more heteroatoms such a halogen atom or other heteroatoms such as O, N, or S.

The aryl sulfur precursor compound is preferably prepared or selected at the highest purity available or has a purity of at least 80% or greater, preferably at least 95% purity or greater. The aryl sulfur precursor compound is preferably substantially moisture-free to avoid the formation of process-damaging HF. Examples of suitable aryl sulfur precursor compounds include 4-nitrophenyl disulfide, 4-nitrophenylsulfenyl chloride, 4-nitrobenzenesulfenyl chloride, 4-bromobenzene thiol, 4-methoxyphenyl disulfide and phenyl disulfide. An example of an aryl sulfur precursor compound with one or more deactivated aromatic rings includes 4-nitrophenyl disulfide. An example of an aryl sulfur precursor compound with one or more active aromatic rings, or oxidatively-sensitive or ring-activating substituents, includes 4-methoxyphenyl disulfide.

The fluorinating agent may be an elemental fluorine gas ("$F_2$"), a fluoroxy (OF) reagent, or a combination thereof. The fluorinating agent is preferably in gaseous form and may include fluorinating agents that are delivered directly to the reaction or reaction mixture as a gas, as a vaporized liquid, a sublimed solid and/or transported by an inert gas. In embodiments wherein an elemental fluorine gas is used, the concentration of $F_2$ may range from 1% to 30%, preferably from 5% to 20%, by weight of $F_2$ with the balance of the gas being composed of one or more inert gases such as $N_2$, $CO_2$, Ar, He, $O_2$, or air. In other embodiments of the present invention, a fluoroxy reagent may be used by itself or in combination with an elemental fluorine gas. Examples of fluoroxy reagents include fluoroxytrifluoromethane ("FTM" or $F_3COF$), bis(fluoroxy)difluoromethane ("BDM" or $F_2C(OF)_2$), $F_5SOF$, or $CsSO_3F$. In certain embodiments wherein the fluoroxy reagent is in gaseous form, the concentration of the fluoroxy reagent can range from 1% to 100%, preferably from 5% to 20% by weight of fluoroxy with the balance of the gas being composed of one or more inert gases such as $N_2$, $CO_2$, Ar, He, $O_2$, or air. In the embodiments wherein a fluoroxy reagent is used in step one, BDM is preferably used for aryl sulfur precursor compounds that have a deactivated ring such as 4-nitrophenyl disulfide and FTM is preferably used for aromatics with oxidatively-sensitive or ring-activating substituents such as 4-methoxyphenyl disulfide. The amount and the selection of fluorinating agent that is added to the reaction or reaction mixture depends upon the reactivity of the reagents contained therein. In certain preferred embodiments, the fluorinating agent is added to the reaction or reaction mixture until substantially all of the aryl sulfur precursor compound is converted to an end-product. In these embodiments, the end-product may not necessarily be the intermediate sulfur trifluoride product.

In step one of the method of the present invention, the at least one aryl sulfur precursor compound may be reacted with the one or more fluorinating agents either neat (i.e., without solvent) or in the presence of one or more solvents. The amount of aryl sulfur precursor compound used in the reaction depends upon the efficacy of the fluorinating agent employed and the general reactivity of the aromatic ring. In embodiments wherein a fluoroxy fluorinating agent is employed, the method of the present invention is conducted neat. In embodiments wherein a solvent is used, the concentration of the aryl sulfur precursor compound in a given solvent or solvent mixture can range from 1% to 99%, preferably from 10% to 70%, and more preferably between 20% and 50% by weight of aryl sulfur precursor compound. The solvent is preferably an inert, non-aqueous solvent. In this regard, the solvent preferably will not substantially react under the reaction conditions and should not contain functionalities (i.e. OH, NH, etc.) that will react with the intermediate sulfurtrifluoride and related chemicals. Suitable solvents include, but are not limited to, halocarbons (e.g. methylene chloride); nitriles (e.g. acetonitrile); fluorocarbons, freons, or fluorinated aromatic compounds (e.g. benzotrifluoride), hydrocarbons (e.g. pentane or hexane), alone or in a mixture thereof. In certain embodiments wherein a less reactive fluorinating agent such as FTM is used, the solvent may comprise a hydrocarbon. In certain preferred embodiments, the solvent is acetonitrile.

The reaction time for the first step may range from about 0 hours or instantaneous to about 72 hours, preferably from about 0 to about 24 hours. The anticipated yield of the intermediate sulfur trifluoride product ranges from about 40% to about 99% of the theoretical yield. In certain embodiments, the intermediate sulfur trifluoride product may be purified by standard procedures such as distillation, chromatography, recrystallization, and/or titration.

In the second step of the reaction, the intermediate sulfur trifluoride product is exposed to one or more fluorinating agents, and optionally a fluoride source, to form the aryl sulfurpentafluoride product. As before, the amount and selection of the fluorinating agent depends upon the reactivity of the fluorinating agent with the reagents in the reaction or reaction mixture. The one or more fluorinating agents used preferably has sufficient reactivity to form the sulfur pentafluoride end-product without excessive ring fluorination, fluorination of the ring substituents, ring-opening, or ejection of the sulfur atom from the ring. In certain embodiments, the fluorinating agent is preferably the same fluorinating agent that was used in conducting the first step. For example, in embodiments wherein a fluoroxy fluorinating agent is used for the first step, the same fluoroxy fluorinating reagent is used for the second step to allow for a certain amount oxidation of the sulfur group without excessive ring fluorination or degradation when substituent oxidation occurs. In some embodiments, the second step may be conducted in the presence of a solvent. Solvents that may be used in the second step include any of the solvents used in the first step. The reaction time for the second step may range from about 0 to about 72 hours or preferably from about 0 to about 24 hours. The anticipated yield of the aryl sulfurpentafluoride compound ranges from about 10% to about 75%, or preferably from about 30% to about 75%, of the theoretical yield. The final product may be purified by standard procedures such as distillation, chromatography, recrystallization, and/or titration.

The reaction temperature for both steps of the reaction may range from $-78°$ C. to the $100°$ C. The reaction temperature is dependent upon the reactivity of the aryl sulfur precursor compound, the one or more fluorinating agents, and/or the intermediate sulfurtrifluoride product. For example, in embodiments wherein an elemental fluorine gas or $F_2$ is used as the fluorinating agent in step one and/or step two of the reaction, the reaction temperatures preferably range from $-35°$ C. to $-15°$ C. in order to avoid ring fluorination and production of HF. In embodiments wherein the fluoroxy reagent BDM is used as the fluorinating agent in step one and/or step two of the reaction, the reaction temperatures range from $-35$ and $50°$ C., preferably from $-15°$ C. to $0°$ C. In embodiments wherein the fluoroxy reagent FTM is used as the fluorinating agent in step one and/or step two of the reaction, the reaction temperatures range from $-78$ and $100°$ C., preferably from $0°$ C. to $70°$ C.

In certain embodiments of the present invention, a fluoride source may be used in the second step of the method of the present invention. The fluoride source is preferably used in addition to the fluorinating agent. The fluoride source may also be present in the first step of the method; however, it is not preferred. The fluoride source is an anhydrous, oxidatively stable salt that displays fluoride activity and is substantially inert under the reaction conditions. Examples of appropriate salts are carbonates, bicarbonates, oxides, halides, sulfates, phosphates, nitrates, or hydroxides. Examples of suitable fluoride sources include but, are not limited to, alkali metal fluorides (e.g. KF or CsF), alkaline earth metal fluorides, transition metal fluorides, substituted ammonium fluorides (e.g. tetramethylammonium fluoride), active fluoride sources (e.g. NOF), etc. Examples of alkali metal, alkaline earth metal, and transition metals are cerium, cobalt, cesium, potassium, sodium, rubidium, lithium, beryllium, magnesium, calcium, barium, and strontium. Preferred fluoride sources include KF or CsF. The fluoride source can be present in the reaction in amounts that range from a catalytic amount, or approximately 1% mole fraction, to about 50 molar equivalents relative to the amount of aryl sulfur precursor compound or the theoretical amount of the intermediate sulfurtrifluoride product. In embodiments wherein the fluoride source is used in the second step, the fluoride source may be present in the reaction in an amount that ranges from a catalytic amount to two molar equivalents, preferably from one to two molar equivalents, relative to the theoretical concentration of the intermediate sulfurtrifluoride product.

The method of the present invention may be used to prepare aryl sulfurpentafluoride having the formula (III) as depicted herein. Exemplary aryl sulfurpentafluoride compounds include, but are not limited to, 4-nitrophenylsulfur pentafluoride, 4-bromophenylsulfur pentafluoride, 4-nitrobenzenesulfurpentafluoride, 3-nitrobenzenesulphurpentafluoride, 2-nitrobenzenesulfurpentafluoride, pyridinesulfurpentafluoride, and 2,3-dichlorpyrdine-5-sulfurpentafluoride.

The aryl sulfurpentafluoride compounds may be used as synthetic intermediates or starting reagents in any organic composition in which the organic composition requires the introduction of $SF_5$ and/or aryl groups into the composition. The compounds may be useful as a starting reagent for a number of derivatives that include, but are not limited to, saturated ethers, vinyl ethers, pyrazoles, cyclic alkenes, and $SF_5$-containing alkenes and alkynes. These compounds may also be used as an attractive alternative to reagents containing the $CF_3$ group. In this connection, the compounds of the present invention can be used as precursors within liquid crystal compositions such as those disclosed in U.S. Pat. Nos. 5,728,319 and 5,792,386 in place of those derivatives containing the $CF_3$ group. The aryl group may be extracted during the preparation of the liquid crystal composition. The compounds of the present invention may also be used within surfactant compositions such as those described, for example, in EP 444822. Further uses for the compounds of the present invention include precursors or reagents within pharmaceutical compositions such as the compositions described, for example, in U.S. Pat. No. 6,136,838.

The compounds of the present invention can be incorporated within polymers such as polyacrylates, polyesters, polyurethanes, polyamides, and polyvinyl ethers made by conventional step-growth, chain-growth, or graft polymerization techniques or processes. In some instances, the ethylenically unsaturated compounds of the present invention can be homopolymerized to make homopolymers or copolymerized with copolymerizable monomers to make random, alternating, block, or graft polymers. In these applications, for example, the aryl group of the compound may either be removed from the polymer composition prior to completion or may remain within the polymer to enhance certain properties of the polymer.

The invention will be illustrated in more detail with reference to the following Examples, but it should be understood that the present invention is not deemed to be limited thereto.

EXAMPLES

The reagents for the following examples were prepared as follows. Anhydrous acetonitrile, manufactured by Aldrich, was used as received. A 98+%, commercial-grade 4-nitrophenyl disulfide reagent was fused under high vacuum to dry and then stored and handled in a nitrogen-purged glove box. The 4-bromophenyl disulfide reagent was prepared by reacting 10 g of 98+% commercial-grade 4-bromobenzene thiol with $I_2$ in 100 g of methanol to precipitate the corresponding disulfide. The disulfide was then isolated by adding 100 mL of water and treating with sodium sulfite, basifying with potassium carbonate, then extracting twice with 20 mL of methylene chloride, and removing the solvent under vacuum to expose the product as light yellow crystals. Commercial-grade, 99+% phenyl disulfide reagent was purified by recrystallization from boiling methanol and then dried by fusing under vacuum. Commercial-grade KF reagent was dried by heating to 300° C. under high vacuum for 48 hours then grinding in a mortal and pestle under a dry nitrogen atmosphere; this process was repeated until a constant mass of KF was achieved. Commercial-grade CsF reagent was dried by fusing at 900° C. under $N_2$; the resulting pellets were pulverized prior to use. All reagents were handled and stored in a nitrogen-purged glove box.

For the following examples, the gas chromatograph ("GC") analyses were carried out on a 30 m×0.25 mm×0.25 μm HP5-MS capillary column. The G.C.M.S. Spectra for the examples were performed on a Hewlett Packard 5890 Series 11 G.C. and 5972 series mass selective detector with a HP-5MS. Samples for the nuclear magnetic resonance (NMR) analysis were prepared by placing the analyte into a 5 mm FEP-lined NMR tube and adding deuteroacetonitrile. NMR analyses for the examples were obtained on a Bruker 500 MHz FTNMR spectrometer operated at 470.67.4 MHz ($^{19}F$), 500.29 MHz ($^1H$). Chemical shifts were referenced to neat in $CFCl_3$($^{19}F$) and -TMS ($^1H$).

Unless otherwise designated, the following examples were conducted in a fluorinated ethylene-propylene ("FEP") reactor that was constructed of 0.75 inch FEP tubing manufactured by Saint-Gobain and heat-sealed at one end. The open end of the tubing is fitted with a stainless steel compression fitting (Swagelok) that was machined to fit inlet and outlet tubes attached to stainless steel needle valves (Swagelok). The reactor inlet was extended to the bottom of the reactor via a 0.25 inch FEP tube capped with a 10 micron filter manufactured by Parr Instrument Corporation) for gas dispersion.

Example 1

Low Temperature Reaction of 4-Nitrophenyl Disulfide with Fluorinating Agent Bis(fluoroxy)methane (BDM) in Acetonitrile Solvent A FEP reactor was charged with 1 g (3.2 mmol) amount of 98%+ 4-nitrophenyl disulfide (1 equivalent) and 10 mL of acetonitrile and externally cooled to −20° C. While agitating, 12.8 mmol of BDM (7% in $N_2/CO_2$) were bubbled through the reaction mixture at a rate of 150 sccm/min. The $^1H$ and $^{19}F$-NMR analyses of the resulting clear/colorless solution indicated that full conversion of the disulfide was attained yielding <1% 4-(pentafluorothio)nitrobenzene, 70% of the intermediate aryl sulfurtrifluoride product 4-nitrophenylsulfur trifluoride, and the balance of sulfur-oxyfluorides. Ring-fluorinated products could not be observed.

Example 2

Exposure of 4-Nitrophenylsulfur Trifluoride to Fluorinating Agent BDM at −20° C. in Acetonitrile Solvent

In a FEP reaction, a reaction mixture containing the intermediate aryl sulfurtrifluoride product, 4-nitrophenylsulfur trifluoride, and the solvent acetonitrile was prepared as described above in Example 1 and maintained at −20° C. While agitating, 32 mmol of BDM (7% in $N_2/CO_2$) was bubbled through the reaction mixture at a rate of 150 sccm/min. The $^1H$ and $^{19}F$-NMR analyses indicated that the product solution contained 5% of the sulfurpentafluoride product 4-nitrophenylsulfur pentafluoride, 60% of the intermediate aryl sulfurtrifluoride product 4-nitrophenylsulfur trifluoride, and the balance sulfur-oxyfluorides. Ring-fluorinated products were not observed.

Example 2 illustrates that exposure of the intermediate aryl sulfurtrifluoride product to the fluorinating agent BDM yielded the aryl sulfurpentafluoride product.

Example 3

Exposure of 4-Nitrophenylsulfur Trifluoride to Fluorinating Agent BDM at 0° C. in Acetonitrile Solvent

In a FEP reactor, a reaction mixture containing the intermediate aryl sulfurtrifluoride product, 4-nitrophenylsulfur trifluoride, and the solvent acetonitrile was prepared as described above in Example 1 and warmed to and maintained at 0° C. While agitating, 32 mmol of BDM (7% in $N_2/CO_2$) was bubbled through the reaction mixture at a rate of 150 sccm/min. The $^1H$ and $^{19}F$-NMR analyses indicated that the product solution contained 7% of the sulfurpentafluoride product 4-nitrophenylsulfur pentafluoride, 55% of the intermediate aryl sulfurtrifluoride product 4-nitrophenylsulfur trifluoride, and the balance sulfur-oxyfluorides. Less then 1% of the products were ring-fluorinated.

When compared to example 2, example 3 illustrates that a higher temperature exposure step slightly increased the yield of the sulfurpentafluoride product. However, although present in low amounts, higher temperatures may also cause undesirable ring fluorination.

Example 4

Exposure of 4-Nitrophenylsulfur Trifluoride to Fluorinating Agent BDM at 20° C. in Acetonitrile Solvent

In a FEP reactor, a reaction mixture containing the intermediate aryl sulfurtrifluoride product, 4-nitrophenylsulfur trifluoride, and the solvent acetonitrile was prepared as described above in Example 1 and warmed to and maintained at 20° C. While agitating, 32 mmol of BDM (7% in $N_2/CO_2$) was bubbled through the reaction mixture at a rate of 150 sccm/min. Yellowing of the reaction mixture was observed during the addition of BDM. The $^1H$ and $^{19}F$-NMR analyses indicated that the product solution contained 8% of the sulfurpentafluoride product 4-nitrophenylsulfur pentafluoride, 55% of the intermediate aryl sulfurtrifluoride product 4-nitrophenylsulfur trifluoride, and the balance sulfur-oxyfluorides. Approximately 8% of the products were ring-fluorinated.

When compared to examples 2 and 3, example 4 illustrates that a higher temperature exposure step slightly increased the yield of the sulfurpentafluoride product. However, the amount of ring-fluorinated products also increased.

Example 5

Exposure of 4-Nitrophenylsulfur Trifluoride to Fluorinating Agent BDM in the Presence of Fluoride Source Potassium Fluoride (KF) at −15° C.

In FEP reactor, a reaction mixture containing the intermediate aryl sulfurtrifluoride product, 4-nitrophenylsulfur trifluoride, was prepared as described above in Example 1 and then warmed to room temperature (approximately 25° C.). Approximately 1 g (17.2 mmol) of the fluoride source KF was added to the reactor; yellowing of the reaction mixture was observed upon addition. The reactor was externally cooled to −15° C. While agitating, approximately 30 mmol of BDM (7% in $N_2/CO_2$) was bubbled through the reaction mixture at a rate of 150 sccm/min. The color subsided immediately upon addition of the BDM. The $^1H$ and $^{19}F$-NMR analyses of the product solution indicated it contained 65% of the sulfur pentafluoride product 4-nitrophenylsulfur pentafluoride and the balance of sulfur-oxyfluorides. Trace amounts of the products were ring-fluorinated.

Example 5 illustrates that the use of the fluoride source KF in addition to the fluorinating agent BDM substantially increased the yield of the sulfur pentafluoride product despite the relatively lower temperatures when compared to examples 2 through 4.

Example 6

Scale up of Examples 2 and 5

A reaction mixture containing 20 g (65 mmol) of 4-nitrophenyl disulfide and 150 mL of acetonitrile was charged into a 300 mL 316 stainless steel Parr reactor equipped with a magnetic stir bar and a 10-micron sparger. The reactor was degassed and cooled to a −20° C. internal temperature with a dry ice/acetone bath and the contents were stirred rapidly. The fluorinating agent BDM (7% in $N_2/CO_2$) was bubbled through the reaction mixture at a rate of 300 sccm/min, while not allowing the temperature of the mixture to exceed −15° C. The BDM addition was continued until BDM could be observed in the FTIR of the reactor effluent (~325 mmol BDM).

The reactor was purged with nitrogen and 20 g (345 mmol) of the fluoride source KF was added to the reaction mixture. The reaction mixture was further treated with approximately 195 mmol BDM (7% in $N_2/CO_2$) at a rate of 150 sccm/min and at −15° C. until full BDM breakthrough was observed in the FTIR of the reactor effluent. The contents of the reactor were poured over 100 g of ice and basified to a pH 14 with an ice-cold 50% aqueous sodium hydroxide to insure conversion of all sulfur oxyfluorides. The solution was then adjusted to a pH<1 using ice-cold concentrated hydrochloric acid then extracted 3 times with heptane. If 3 layers are observed during the extraction, more acid is slowly added in until only 2-layers are present. The organic layers were combined, passed through a bed of Norit SX-2 activated carbon and a bed of magnesium sulfate, then was evaporated down to 50 mL of total liquid. The resulting light-yellow solution was cooled to −30° C. allowing the product to crystallize as light-yellow plates. The crystals were retrieved by vacuum filtration and dried in air yielding 20.4 g (82 mmol, 63% yield based on disulfide) of highly pure 4-nitrophenylsulfur pentafluoride (uncorrected melting point 37° C.–38° C., lit. 37° C.). The $^1H$-NMR, $^{19}F$-NMR, and GC-MS analysis of the product indicated the presence of less than 1% ring fluorination.

Example 6 illustrates that the results of example 5 can be achieved on a larger scale.

Example 7

Reaction of 4-Nitrophenyl Disulfide with Fluoride Source KF in Acetonitrile Solvent and Exposure to Fluorinating Agent BDM A FEP reactor was charged with 1 g (3.2 mmol) of 4-nitrophenyl disulfide, 1 g (17.2 mmol) of KF, and 10 mL of acetonitrile. The reactor was externally cooled to −20° C. using a dry ice/acetone bath. While agitating, 32 mmol of BDM (7% in $N_2/CO_2$) was bubbled through the reaction mixture at a rate of 150 sccm/min, not allowing the temperature to exceed −15° C. GC-MS analysis immediately identified a presence of minimal amounts of sulfur pentafluoride product and 7–8% ring fluorination.

When compared to example 2, the use of a fluoride source rather than a fluorinating agent in the initial reaction mixture did not yield the sulfur pentafluoride product. Further, ring fluorination occurred in the present example whereas in example 2, a similar reaction without a fluoride source, ring fluorination did not.

Example 8

Reaction of 4-Nitrophenylsulfenyl Chloride with Fluorinating Agent BDM in Acetonitrile Solvent and Exposure to Fluorinating Agent BDM and Fluoride Source Cesium Fluoride (CsF)

A FEP reactor was charged with 1 g (5.3 mmol) of commercial 95% (tech.) 4-nitrobenzenesulfenyl chloride and 10 mL of acetonitrile were charged to an FEP reactor. The reactor was externally cooled to −20° C. using a dry ice/acetone bath. While agitating, 20 mmol of BDM (7% in $N_2/CO_2$) was bubbled through the reaction mixture at a rate of 150 sccm/min, not allowing the temperature to exceed −15° C. During the fluorination, chlorine and chlorine oxides were observed by UV-Vis in the reactor effluent. The fluorination was halted as soon as BDM breakthrough was observed and all chlorine species were absent from the reactor effluent.

In a nitrogen-purged glove box, 1 g (6.6 mmol) of anhydrous CsF was added to the reaction mixture, which immediately changed to dark yellow. The resulting mixture was agitated and treated further with BDM at a flow rate of 150 sccm/min until full BDM breakthrough was observed in the FTIR of the reactor effluent (13.8 mmol additional BDM). $^1$H-NMR and $^{19}$FNMR analyses of the product mixture indicated an approximate 65% presence of the sulfur pentafluoride product 4-nitrophenylsulfur pentafluoride and less than 1% ring fluorination for all observable species with the balance being mainly composed of sulfur oxyfluorides.

Compared to example 7, example 8 illustrates that the use of the fluoride source in addition to the fluorinating agent during the exposure step, rather than during the initial reaction, results in a relatively higher yield of sulfur pentafluoride product. Example 8 also illustrates that other halide reagents, such as 4-nitrophenylsulfenyl chloride may be used to produce the sulfur pentafluoride product. The generation of chlorine oxides during processing, however, may present a safety issue in the manufacturability of the end product.

Example 9

Reaction of 4-Nitrobenzenesulfenyl Chloride with Fluorinating Agent BDM in Acetonitrile Solvent then Exposure to Fluorinating Agent $F_2$ and Fluoride Source CsF A FEP reactor was charged with 1 g (5.3 mmol) of commercial 95% (tech.) 4-nitrobenzenesulfenyl chloride and 10 mL of acetonitrile. The reactor was externally cooled to −20° C. using a dry ice/acetone bath. While agitating, 20 mmol of BDM (7% in $N_2/CO_2$) was bubbled through the reaction mixture at a rate of 150 sccm/min, not allowing the temperature to exceed −15° C. During the fluorination, chlorine and chlorine oxides were observed by UV-Vis in the reactor effluent. The fluorination was halted as soon as BDM breakthrough was observed and all chlorine species were absent from the reactor effluent.

In a nitrogen-purged glove box, 1 g (6.6 mmol) of anhydrous CsF was added to the reaction mixture, which immediately changed to dark yellow. The resulting mixture was cooled and maintained between −25 and −30° C. while agitating and treating further with $F_2$ (5% in $N_2$) at a flow rate of 150 sccm/min until full $F_2$ breakthrough was observed in the UV-Vis of the reactor effluent (16 mmol $F_2$ added). $^1$H-NMR and $^{19}$FNMR analysis of the product mixture indicated an approximate 75% presence of 4-nitrophenylsulfur pentafluoride and less than 1% ring fluorination for all observable species with the balance being composed mostly of the arylsulfur trifluoride.

Compared to example 8, example 9 illustrates that the use of the fluorinating agent $F_2$ during the exposure step may provide a higher yield than the BDM fluorinating agent.

Comparative Example 10

Fluorination According to Prior Art (WO9705106)

A FEP reactor was charged with 1 g (3.2 mmol) of 4-nitrophenyl disulfide and 15 mL of acetonitrile. The reactor was externally cooled to −7° C., and 10% $F_2$ in $N_2$ was bubbled through the slurry at a flow rate of 150 sccm/min. Small flashes of light were observed during the fluorination of the slurry but subsided once the system was homogeneous. The fluorination was stopped after 42 mmol (13 equivalents) of $F_2$ had been passed through the reactor leaving a dark-yellow solution. $^1$H-NMR and $^{19}$F-NMR analysis of the resulting solution indicated that approximately 40% of observable species were present as nitrophenylsulfur pentafluoride compounds (including ring-fluorinated) and 7–8% represented total ring fluorinated products.

Compared to the present invention, comparative example 10 illustrates that direct fluorination of the reaction mixture resulted in a lower yield of the sulfur pentafluoride product and a higher amount of ring fluorinated products. Further, the flashes of light during the process indicated that $F_2$ was reacting in an uncontrolled manner with particles in the slurry.

Example 11

Reaction of 4-Nitrophenyl Disulfide with Fluorinating Agent $F_2$ in Acetonitrile Solvent then Exposure to $F_2$ with CsF Fluoride Source A FEP reactor was charged with 1 g (3.2 mmol) of 4-nitrophenyl disulfide and 10 mL of acetonitrile. The reactor was cooled to −35° C. using a dry ice/acetone bath. While agitating, 5% $F_2$ in $N_2$ was bubbled through the reaction mixture at a flow rate of 150 sccm/min and the temperature was maintained below −25° C. The fluorination was continued until $F_2$ breakthrough was observed in the UV-Vis of the reactor effluent (22 mmol of $F_2$). $^1$H and $^{19}$F-NMR of the resultant product mixture indicated 11% nitrophenylsulfur pentafluoride, 70% nitrophenylsulfur trifluoride, and a balance composed mostly of ring fluorinated material (5%), sulfur oxyfluorides, and the starting disulfide.

In a nitrogen-purged glove box, 1 g (6.6 mmol) of anhydrous CsF was added to the reactor and the reactor was cooled to and maintained at a temperature ranging between −25° C. and −30° C. The fluorination of the reaction mixture was continued by adding 30 mmol more $F_2$ at a flow rate of 150 sccm/min while agitating. NMR analysis indicated that approximately 40% of observable species consisted of the desired 4-nitrophenylsulfur pentafluoride product with the balance being composed of the sulfur trifluoride adduct, ring fluorinated products totaling 5%, and sulfur oxyfluorides.

Example 12

Reaction of Nitrobenzenesulfenyl chloride with Fluorinating Agent $F_2$ in Acetonitrile Solvent then Exposure to $F_2$ with CsF Fluoride Source A FEP reactor was charged with 1 g (5.3 mmol) of commercial 95% (tech.) 4-nitrobenzenesulfenyl chloride and 10 mL of acetonitrile. The reactor was externally cooled to −35° C. using a dry ice/acetone bath. While agitating, 5% $F_2$ in $N_2$ was bubbled through the reaction mixture at a flow rate of 150 sccm/min and the temperature was maintained below −25° C. $Cl_2$ was observed in the UV-Vis of the reactor effluent during the fluorination. The fluorination was stopped when full $F_2$ breakthrough and complete absence of $Cl_2$ were observed in the UV-Vis of the reactor effluent (11 mmol $F_2$). GC-MS analysis indicated less than 5% nitrophenylsulfur pentafluoride and approximately 5% ring fluorination.

In a nitrogen-purged glove box, 1 g (6.6 mmol) of CsF was added to the reactor in a nitrogen-purged glove box and the reactor contents were agitated and fluorinated further with 5% $F_2$ in $N_2$ at a flow rate of 150 sccm/min and a temperature of −25° C. The fluorination was continued until full $F_2$ breakthrough was observed in the UV-Vis of the reactor effluent (21 mmol more $F_2$). $^1$H and $^{19}$F-NMR indicated an approximate 10% presence of 4-nitrophenylsulfur pentafluoride and 7–8% ring fluorinated products; while the corresponding sulfur trifluoride was present, the major product observed by NMR was not identified.

Compared to example 11, the present example illustrates that the use of a chlorine-containing reagent rather than a fluorine-containing reagent in the initial reaction mixture resulted in a lower yield of the sulfur pentafluoride product and a higher amount of ring fluorinated products.

Example 13

Reaction of 4-Bromobenzene Thiol with $F_2$ in HF

A FEP reactor was charged with 1.15 g (6.1 mmol) 4-bromobenzene thiol and 20 mL anhydrous HF and maintained at −20° C. using a dry ice/acetone bath. Undissolved solid and a pale yellow mixture were observed at −30° C. While agitating, 35 mmol $F_2$ (10% $F_2$ in air) was bubbled through the reaction mixture at a flow rate of 100 sccm/min. Initially, the mixture turned dark purple, but after addition of 18 mmol $F_2$, a homogeneous yellow mixture was observed. Upon completion of the $F_2$ addition, the mixture was colorless. Evacuation of HF left a free-flowing white solid. NMR analysis of the white solid revealed ~90% phenyl $SF_3$ and SOF containing products, but 70% of this material proved to be highly reactive difluorobromine phenyl $SF_3$/SOF complexes (see FIG. 1). Only traces of $SF_5$ containing material were observed along with ~5% ring fluorination products.

The fluorinating agent $F_2$ fluorinates the bromine atom thereby producing a dangerously unstable material as well as fluorinates the ring pendant atoms and/or the ring itself. Further, HF is detrimental to the formation of $SF_5$.

Example 14

Reaction of 4-Bromobenzene Thiol with BDM in HF

A FEP reactor was charged with 1 g (5.3 mmol) of 4-bromobenzene thiol. A 15 g amount of anhydrous HF was distilled into the reactor under static vacuum. The reactor was maintained at −20° C. using a dry ice/acetone bath. While agitating, BDM (7% in $N_2/CO_2$) was bubbled through the reaction mixture at a flow rate of 150 sccm/min. A purple color persisted throughout most of the fluorination. The reaction was halted after adding 15.9 mmol (3 equivalents relative to thiol) BDM. The HF was removed from the mixture under vacuum at −25° C. revealing an orange oil. $^1$H and $^{19}$F-NMR analyses of the product mixture indicated only the corresponding sulfur trifluoride and disulfide as major products containing traces of sulfur oxyfluorides. No bromine fluorides were detected.

In comparison with example 13, the present illustrates that unlike the $F_2$ fluorinating agent, the BDM fluorinating agent does not fluorinate the bromine atom or produce a dangerously unstable material. In addition, this example also demonstrates that HF is detrimental to the formation of $SF_5$.

Example 15

Reaction of 4-Bromophenyl Disulfide with BDM in Acetonitrile

A FEP reactor was charged with 1 g (2.8 mmol) of 4-bromophenyl disulfide and 10 mL of acetonitrile and then externally cooled with a dry ice/acetone bath to −15° C. While agitating, BDM (7% in $N_2/CO_2$) was bubbled through the reaction mixture at a flow rate of 150 sccm/min. The reaction mixture changed to dark purple for the majority of the fluorination. The reaction was stopped when full BDM breakthrough was observed in the FTIR of the reactor effluent (11 mmol of BDM). $^1$H and $^{19}$F-NMR analysis of the reaction mixture revealed only a trace of 4-bromophenylsulfur pentafluoride, mostly the corresponding sulfur trifluoride, and approximately 5% of the difluorobromine phenyl $SF_3$/SOF complexes as mentioned in Example 13. Only traces of ring fluorination were observed.

Example 16

Reaction of 4-Bromophenyl Disulfide with Fluorinating Agent Fluoroxytrifluoromethane (FTM) in Acetonitrile at 50° C.

A FEP reactor was charged with 1 g (2.7 mmol) of 4-bromophenyl disulfide and 15 g of acetonitrile. The reactor was placed in a 50° C. bath. While agitating, approximately 95 mmol of FTM (7% in nitrogen) was bubbled through the reaction mixture at a flow rate of 200 sccm/min. $^{19}$F-NMR analysis of the product mixture indicated approximately 15% of observable species was 4-bromophenylsulfur pentafluoride with a balance composed of its ring fluorinated derivatives and a majority of unidentified products. No organobromine fluorides were detected.

Example 17

Reaction of 4-Bromophenyl Disulfide with Fluorinating Agent FTM in Acetonitrile at 70° C.

A FEP reactor was charged with 2.5 g (6.6 mmol) of 4-bromophenyl disulfide and 15 g of acetonitrile. The reactor was placed in a 60° C. bath and the contents were treated with approximately 240 mmol of FTM (7% in nitrogen) at a flow rate of 200 sccm/min as the bath temperature was increased to 70° C. during the fluorination. Much of the solvent was carried away in the effluent during the reaction. $^{19}$F-NMR analysis of the product mixture indicated approximately 10% of observable species was 4-bromophenylsulfur pentafluoride with a balance composed of its ring fluorinated derivatives and a majority of unidentified products. No organobromine fluorides were detected.

Compared to example 16, the relatively higher temperature reaction of 4-bromophenyl disulfide with FTM resulted in a slight decrease in yield of the sulfurpentafluoride product.

Example 18

Reaction of 4-Bromophenyl Disulfide with Fluorinating Agent FTM in Acetonitrile at 100° C.

A FEP reactor was charged with 2.5 g (6.6 mmol) of 4-bromophenyl disulfide and 15 g of acetonitrile. The reactor was placed in a 60° C. bath and the contents were treated with approximately 240 mmol of FTM (7% in nitrogen) at a flow rate of 200 sccm/min as the bath temperature was increased to 100° C. during the fluorination. All of the solvent was carried away in the effluent during the reaction. $^{19}$F-NMR analysis of the product mixture indicated approximately 10% of observable species was 4-bromophenylsulfur pentafluoride with a balance composed of its ring fluorinated derivatives and a majority of unidentified products. No organobromine fluorides were detected.

Compared to example 17, the relatively higher temperature reaction of 4-bromophenyl disulfide with FTM did not increase the yield of the sulfurpentafluoride product.

Example 19

Reaction of 4-Bromophenyl Disulfide and Fluoride Source CsF with Fluorinating Agent FTM in Acetonitrile at 70° C.

A FEP reactor was charged with 2.5 g (6.6 mmol) of 4-bromophenyl disulfide, 2.5 g (16.4 mmol) of CsF, and 15 g of acetonitrile. The reactor was placed in a 60° C. bath and the contents were treated with approximately 240 mmol of FTM (7% in nitrogen) at a flow rate of 200 sccm/min as the bath temperature was increased to 70° C. during the fluorination. Much of the solvent was carried away in the effluent during the reaction. $^{19}$F-NMR analysis of the product mixture indicated approximately 17% of observable species was 4-bromophenylsulfur pentafluoride with a balance composed of its ring fluorinated derivatives and a majority of unidentified products. No organobromine fluorides were detected.

Compared to example 17, the presence of the fluoride source in the reaction mixture resulted in a slight increase in yield of the sulfurpentafluoride product.

Example 20

Reaction of 4-Bromophenyl Disulfide with FTM in Acetonitrile at 20° C. then with $F_2$ at −30° C.

A FEP reactor was charged with 1 g (2.7 mmol) of 4-bromophenyl disulfide and 15 g of acetonitrile. While agitating, FTM (7% in nitrogen) was bubbled through the reaction mixture at room temperature and a flow rate of 200 sccm/min until full FTM breakthrough was observed in the FTIR of the reactor effluent (no count obtained). The reactor was externally cooled to −30° C. and the reactor contents were treated further with 20% $F_2$ in $N_2$ (no count obtained). $^{19}$F-NMR analysis of the product mixture indicated approximately 30% of observable species was 4-bromophenylsulfur pentafluoride with a balance composed of its ring fluorinated and sulfur oxyfluoride derivatives. Traces of bromine fluorides were observed.

Compared to the previous examples 16 through 18, the present example illustrates that the lower temperature reaction and exposure to a $F_2$ fluorinating agent resulted in a higher yield of the sulfur pentafluoride product.

Example 21

Reaction of 4-Bromophenyl Disulfide with FTM in Acetonitrile at 20° C.

A FEP reactor was charged with 1 g (2.7 mmol) of 4-bromophenyl disulfide and 10 mL of acetonitrile. While agitating, FTM (7% in nitrogen) was bubbled through the reaction mixture at a flow rate of 200 sccm/min until full FTM breakthrough was observed in the FTIR of the reactor effluent (7.1 mmol FTM). $^1$H and $^{19}$F-NMR analysis indicated only a 70% conversion of the starting material to approximately 5% 4-bromophenylsulfur pentafluoride, 60% 4-bromophenylsulfur trifluoride, with a balance of oxyfluorides and unidentified species; no ring fluorination or bromine fluorides were observed. 1 g (17.2 mmol) of anhydrous KF was added to the reactor and the reactor contents were treated further with 27 mmol more FTM. NMR analysis indicated no change in product composition.

Compared to example 20, the present example, which did not include exposure to a $F_2$ fluorinating agent, resulted in a lower yield of the sulfur pentafluoride product.

Example 22

Reaction of 4-Bromophenyl Disulfide with FTM at 20° C. then Exposure to Fluoride Source CsF and Fluorinating Agent BDM at −10° C.

A FEP reactor was charged with 1 g (2.7 mmol) of 4-bromophenyl disulfide and 15 g of acetonitrile. While agitating, FTM (7% in nitrogen) was bubbled through the reaction mixture at a flow rate of 200 sccm/min and at a temperature of 20° C. until full FTM breakthrough was observed in the FTIR of the reactor effluent (9.5 mmol FTM).

The reactor contents were purged with $N_2$. A quantity of 1 g of (6.6 mmol) CsF was added to the reaction mixture, cooled to −15° C., and then treated with 8.2 mmol of BDM (7% in $N_2$) at a flow rate of 150 sccm/min while agitating. $^1$H- and $^9$F-NMR analyses indicated that approximately 35% of observable species was 4-bromophenylsulfur pentafluoride with a balance composed mostly of sulfuroxy fluoride derivatives and a trace of ring-fluorinated products. No organobromine fluorides were detected. However, their presence could not be ruled out since it is possible that such products may form insoluble complexes with CsF.

Compared to example 21, the present example, which included the step of exposing the reaction mixture to BDM and CsF after reaction of the 4-bromophenyl disulfide reagent with FTM, resulted in a higher yield of the sulfur pentafluoride product.

While the invention has been described in detail and with reference to specific examples thereof, it will be apparent to one skilled in the art that various changes and modifications can be made therein without departing from the spirit and scope thereof.

What is claimed is:

1. A process for preparing an aryl sulfurpentafluoride compound having a formula (III) as follows:

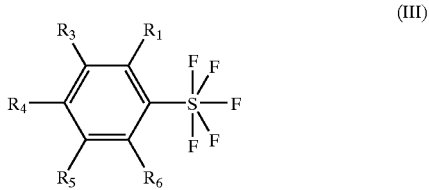

the process comprising:
  combining an at least one aryl sulfur compound having a formula (Ia) or a formula (Ib) as follows:

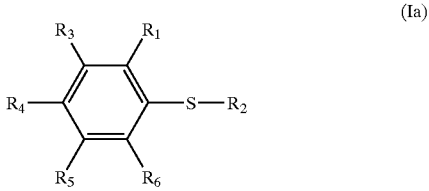

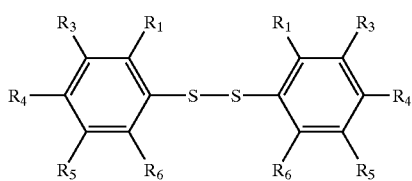

with a fluorinating agent to at least partially react and form an intermediate aryl sulfurtrifluoride product wherein the fluorinating agent is at least one member selected from the group consisting of an elemental fluorine gas, a fluoroxy reagent, or a combination thereof; and
  exposing the intermediate aryl sulfurtrifluoride product to the fluorinating agent and a fluoride source to at least partially react and form the aryl sulfurpentafluoride compound;
  wherein $R_1$, $R_3$, $R_4$, $R_5$, and $R_6$ are each independently a hydrogen atom; a halogen atom; a linear alkyl group having a number of C atoms that range from 1 to 18; a branched alkyl group having a number of C atoms that range from 3 to 18; a cyclic alkyl group having a number of C atoms that range from 3 to 18; an aryl group having a number of C atoms that range from 6 to 30; an alkoxy group having a number of C atoms that range from 1 to 18; $NO_2$; a perfluoroalkyl group having a number of C atoms that range from 1 to 18; $SF_5$; $SO_2F$; or a CN group; and
  wherein $R_2$ is a hydrogen atom or a halogen atom.

2. The method of claim 1 wherein the combining and the exposing steps are performed in the same reaction vessel.

3. The method of claim 1 wherein the combining step is conducted in the presence of a solvent.

4. The method of claim 3 wherein the weight percentage of the aryl sulfur compound to the weight percentage of the solvent ranges from 10% to 70%.

5. The method of claim 4 wherein the weight percentage of the aryl sulfur compound to the weight percentage of solvent ranges from 20% to 50%.

6. The method of claim 1 wherein the fluorinating agent is the fluorine gas.

7. The method of claim 6 wherein the fluorine gas comprises from 1 to 30 weight percent of the fluorine gas and from 70 to 99 weight percent of an inert gas.

8. The method of claim 7 wherein the fluorine gas comprises from 5 to 20 weight percent of the fluorine gas and from 80 to 95 weight percent of the inert gas.

9. The method of claim 1 wherein the fluorinating agent is the fluoroxy reagent.

10. The method of claim 9 wherein the fluoroxy reagent is bis(fluoroxy)methane.

11. The method of claim 10 wherein a temperature of the combining and/or the exposing step ranges from −35° C. to 50° C.

12. The method of claim 11 wherein a temperature of the combining and/or the exposing step ranges from −15° C. to 0° C.

13. The method of claim 9 wherein the fluoroxy reagent is fluoroxytrifluoromethane.

14. The method of claim 13 wherein a temperature of the combining and/or the exposing step ranges from −78° C. to 100° C.

15. The method of claim 14 wherein a temperature of the combining and/or the exposing step ranges from 0° C. to 70° C.

16. The method of claim 1 wherein the exposing step is conducted in the presence of a solvent.

17. The method of claim 1 wherein the fluoride source is at least one member selected from the group consisting of an alkali metal fluoride, a substituted ammonium fluoride, a transition metal fluoride, an alkaline earth metal fluoride, an activated fluoride salt, or a mixture thereof.

18. A process for preparing an aryl sulfurpentafluoride compound having a formula (III) as follows:

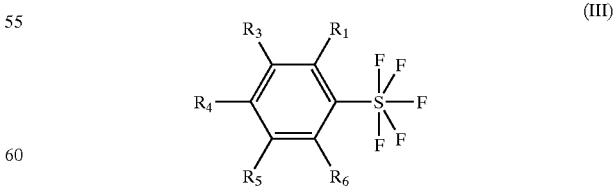

the process comprising:
  providing a mixture comprising from 1 to 70 weight percent of an at least one aryl sulfur compound having a formula (Ia) or a formula (Ib) as follows:

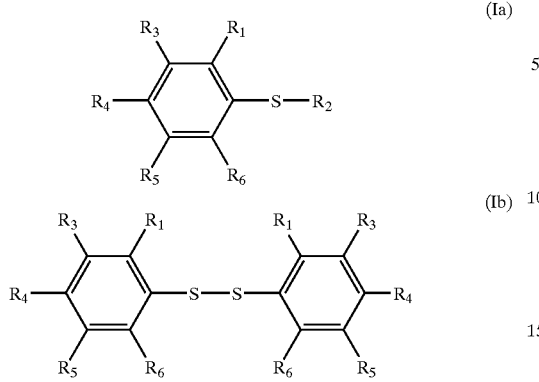

and from 30 to 99 weight percent of a solvent;
  introducing a fluorinating agent to the mixture to form an intermediate aryl sulfurtrifluoride product wherein the fluorinating agent is at least one member selected from the group consisting of an elemental fluorine gas, a fluoroxy reagent, or a combination thereof; and
  exposing the intermediate aryl sulfurtrifluoride product to the fluorinating agent and a fluoride source to at least partially react and form the aryl sulfurpentafluoride compound;
  wherein $R_1$, $R_3$, $R_4$, $R_5$, and $R_6$ are each independently a hydrogen atom; a halogen atom; a linear alkyl group having a number of C atoms that range from 1 to 18; a branched alkyl group having a number of C atoms that range from 3 to 18; a cyclic alkyl group having a number of C atoms that range from 3 to 18; an aryl group having a number of C atoms that range from 6 to 30; an alkoxy group having a number of C atoms that range from 1 to 18; $NO_2$; a perfluoroalkyl group having a number of C atoms that range from 1 to 18; $SF_5$; $SO_2F$; or a CN group; and
  wherein $R_2$ is a hydrogen atom or a halogen atom.

19. The process of claim 18 wherein the fluorinating agent in the introducing step and the exposing step are the same.

20. The process of claim 18 wherein the fluorinating agent in the introducing step and the exposing step are different.

21. The process of claim 18 wherein the mixture further comprises a fluoride source.

22. A process for preparing an aryl sulfurpentafluoride compound having a formula (III) as follows:

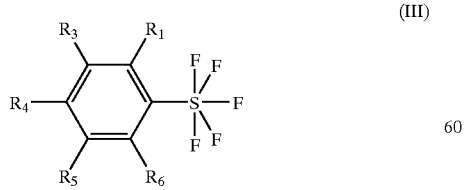

the process comprising:
  combining an at least one aryl sulfur compound having a formula (Ia) or a formula (Ib) as follows:

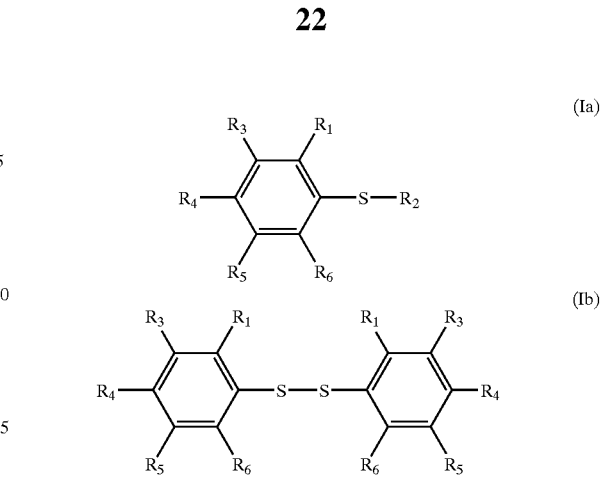

with a fluoroxy reagent to at least partially react and form an intermediate aryl sulfurtrifluoride product; and
  exposing the intermediate aryl sulfurtrifluoride product to the fluoroxy reagent to at least partially react and form the aryl sulfurpentafluoride compound;
  wherein $R_1$, $R_3$, $R_4$, $R_5$, and $R_6$ are each independently a hydrogen atom; a halogen atom; a linear alkyl group having a number of C atoms that range from 1 to 18; a branched alkyl group having a number of C atoms that range from 3 to 18; a cyclic alkyl group having a number of C atoms that range from 3 to 18; an aryl group having a number of C atoms that range from 6 to 30; an alkoxy group having a number of C atoms that range from 1 to 18; $NO_2$; a perfluoroalkyl group having a number of C atoms that range from 1 to 18; $SF_5$; $SO_2F$; or a CN group; and
  wherein $R_2$ is a hydrogen atom or a halogen atom.

23. The method of claim 22 wherein the exposing step further comprises exposing to a fluorine gas.

24. The method of claim 22 wherein the exposing step further comprises exposing to a fluoride source.

25. A process for preparing an aryl sulfurpentafluoride compound having a formula (III) as follows:

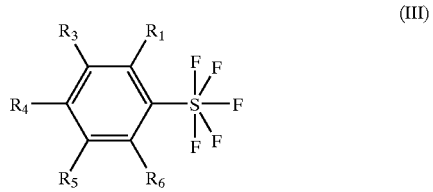

the process comprising:
  combining an at least one aryl sulfur compound having a formula (Ia) or a formula (Ib) as follows:

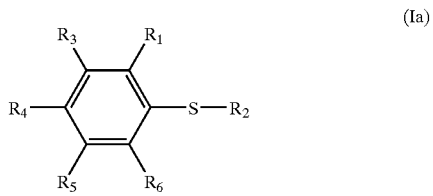

-continued

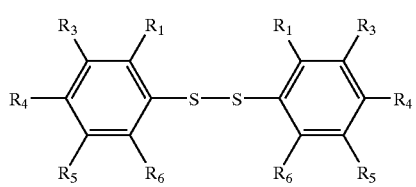
(Ib)

with a first fluorinating agent comprising a fluoroxy reagent to at least partially react and form an intermediate aryl sulfurtrifluoride product; and exposing the intermediate aryl sulfurtrifluoride product to a second fluorinating agent wherein the second fluorinating agent comprises at least one member selected from the group consisting of an elemental fluorine gas, the fluoroxy reagent, and a combination thereof and a fluoride source to at least partially react and form the aryl sulfurpentafluoride compound wherein the yield of the aryl sulfurpentafluoride compound is greater than 40% and/or had less than 1% of ring fluorination;

wherein $R_1$, $R_3$, $R_4$, $R_5$, and $R_6$ are each independently a hydrogen atom; a halogen atom; a linear alkyl group having a number of C atoms that range from 1 to 18; a branched alkyl group having a number of C atoms that range from 3 to 18; a cyclic alkyl group having a number of C atoms that range from 3 to 18; an aryl group having a number of C atoms that range from 6 to 30; an alkoxy group having a number of C atoms that range from 1 to 18; $NO_2$; a perfluoroalkyl group having a number of C atoms that range from 1 to 18; $SF_5$; $SO_2F$; or a CN group; and wherein $R_2$ is a hydrogen atom or a halogen atom.

* * * * *